United States Patent
Winkler et al.

(10) Patent No.: US 12,157,716 B2
(45) Date of Patent: Dec. 3, 2024

(54) MEROCYANINE CRYSTALLIZATION PROCESS

(71) Applicant: BASF SE, Ludwigshafen am Rhein (DE)

(72) Inventors: Barbara Winkler, Schweizerhalle (CH); Levente Simon, Münchwilen (CH)

(73) Assignee: BASF SE, Ludwigshafen am Rhein (DE)

( * ) Notice: Subject to any disclaimer, the term of this patent is extended or adjusted under 35 U.S.C. 154(b) by 918 days.

(21) Appl. No.: 17/259,538

(22) PCT Filed: Jul. 9, 2019

(86) PCT No.: PCT/EP2019/068358
§ 371 (c)(1),
(2) Date: Jan. 11, 2021

(87) PCT Pub. No.: WO2020/011766
PCT Pub. Date: Jan. 16, 2020

(65) Prior Publication Data
US 2021/0323912 A1    Oct. 21, 2021

(30) Foreign Application Priority Data
Jul. 12, 2018   (EP) ..................... 18183223

(51) Int. Cl.
*C07C 253/34* (2006.01)
*A61K 8/02* (2006.01)
*A61K 8/44* (2006.01)
*A61Q 17/04* (2006.01)

(52) U.S. Cl.
CPC .......... *C07C 253/34* (2013.01); *A61K 8/0245* (2013.01); *A61K 8/44* (2013.01); *A61Q 17/04* (2013.01); *A61K 2800/26* (2013.01); *A61K 2800/60* (2013.01); *A61K 2800/805* (2013.01); *C07C 2601/16* (2017.05)

(58) Field of Classification Search
CPC ........................ C07C 253/34; C07B 2200/13
See application file for complete search history.

(56) References Cited

U.S. PATENT DOCUMENTS

| | | | |
|---|---|---|---|
| 2,211,762 A * | 8/1940 | Brooker | C09B 23/10 546/276.1 |
| 2,493,748 A * | 1/1950 | Brooker | C09B 23/0075 548/312.1 |
| 2,728,766 A * | 12/1955 | Knott | C09B 23/105 546/175 |
| 4,749,643 A | 6/1988 | Ohlschlager et al. | |
| 2010/0035839 A1 | 2/2010 | Wagner | |
| 2011/0200540 A1 | 8/2011 | Wagner et al. | |
| 2014/0150380 A1 | 6/2014 | Winkler et al. | |
| 2014/0294743 A1 | 10/2014 | Richard et al. | |
| 2015/0335556 A1 | 11/2015 | Roudot et al. | |
| 2015/0366769 A1 | 12/2015 | Roudot et al. | |

FOREIGN PATENT DOCUMENTS

| | | | | |
|---|---|---|---|---|
| CN | 1897911 A | 1/2007 | | |
| CN | 103917218 A | 7/2014 | | |
| CN | 105050573 A | 11/2015 | | |
| CN | 105188646 A | 12/2015 | | |
| CN | 105188653 A | 12/2015 | | |
| CN | 105188654 A | 12/2015 | | |
| CN | 105431130 A | 3/2016 | | |
| CN | 105705131 A | 6/2016 | | |
| FR | 3046929 A1 | 7/2017 | | |
| GB | 2445635 A | 7/2008 | | |
| IN | 105307631 A | 2/2016 | | |
| JP | 62-056957 A | 3/1987 | | |
| JP | 62-273841 A | 11/1987 | | |
| JP | 03-230155 A | 10/1991 | | |
| JP | 2009-067973 A | 4/2009 | | |
| JP | 2009-120653 A | 6/2009 | | |
| JP | 2010-536822 A | 12/2010 | | |
| JP | 2014-527039 A | 10/2014 | | |
| JP | 2014-529337 A | 11/2014 | | |
| WO | WO-2004006878 A1 * | 1/2004 | ............... | A61K 8/40 |
| WO | 2007/071582 A1 | 6/2007 | | |
| WO | 2009/027258 A2 | 3/2009 | | |
| WO | 2013/011480 A1 | 1/2013 | | |
| WO | WO-2013010590 A1 * | 1/2013 | ............... | A61K 8/41 |
| WO | 2014/111563 A2 | 7/2014 | | |
| WO | 2014/111566 A2 | 7/2014 | | |
| WO | 2014/111567 A2 | 7/2014 | | |
| WO | 2014/111568 A1 | 7/2014 | | |
| WO | 2014/111569 A2 | 7/2014 | | |

(Continued)

OTHER PUBLICATIONS

Winkler et al., Tetrahedron Letters (2014), 55(10), 1749-1751. (Year: 2014).*

(Continued)

*Primary Examiner* — Laura L Stockton
(74) *Attorney, Agent, or Firm* — Faegre Drinker Biddle & Reath LLP

(57) ABSTRACT

The present invention relates to a process for preparing a crystalline merocyanine compound, comprising the step of dissolving a merocyanine compound in an organic, polar solvent, wherein the process is performed at a pH below than 7 in the presence of an acid, wherein residual levels of colored impurities are eliminated.

13 Claims, No Drawings

(56) References Cited

FOREIGN PATENT DOCUMENTS

| WO | 2017/129669 A1 | 8/2017 |
| WO | 2017/129670 A1 | 8/2017 |
| WO | 2017/129673 A1 | 8/2017 |
| WO | 2017/129674 A1 | 8/2017 |

OTHER PUBLICATIONS

"Process for producing 3-Aminocyclohex-2-en-1-ylidene Compounds", Technical Disclosure-Prior Art Database, ip.com, IPCOM000225139D, Jan. 25, 2013, 42 pages.
European Search Report for EP Patent Application No. 18183223.9, Issued on Jan. 21, 2019, 3 pages.
International Preliminary Report on Patentability received for PCT Patent Application No. PCT/EP2019/068358, mailed on Jan. 21, 2021, 9 pages.
International Search Report and Written Opinion received for PCT Patent Application No. PCT/EP2019/068358, mailed on Aug. 14, 2019, 11 pages.

* cited by examiner

MEROCYANINE CRYSTALLIZATION PROCESS

CROSS-REFERENCE TO RELATED APPLICATIONS

This application is a national stage application (under 35 U.S.C. § 371) of PCT/EP2019/068358, filed Jul. 9, 2019, which claims benefit of European Application No. 18183223.9, filed Jul. 12, 2018.

The present invention provides an improved crystallization process for merocyanine compounds in high purity and improved color properties. The process for preparing a crystalline merocyanine comprises the step of dissolving a merocyanine compound in an organic, polar solvent, wherein the process is performed at a pH below 7.

3-Amino-2-cyclohexan-1-ylidene derivatives represented by the following formula (1) belong to the chemical group of merocyanines and are useful as UV absorbers for protecting household products from photolytic and oxidative degradation, as plastic additives, preferably for food and pharmaceutical packaging applications, for preventing photo-degradation of food by incorporation of these compounds into transparent food containers, for protection of UV-A sensitive drugs from photo-degradation by incorporation of UV absorber in transparent blister foils or transparent pharmacy containers, as additives for photographic and printing applications, as additives for electronic applications and for protecting the ingredients in agriculture applications.

The merocyanine derivatives according to the present invention are produced via a multi-step sequence which is affected with the formation of colored by-products. The colored impurities have the disadvantage of causing an unwanted discoloration in the final commercial application. The unwanted discoloration is typically observed as a yellowing in the final commercial product e.g. a sunscreen cream formulation or packaging. The ability of the merocyanine product containing said impurities to discolor the final product correlates with its original color before it is incorporated into the final product. The color of the merocyanine product can be determined by colorimetric measurements. Among these the determination of the Gardner Index is a common method to determine particularly the yellowness of a substance. Merocyanine product samples with higher content of colored impurities display higher Gardner Index values and cause more pronounced discolorations of the final commercial product form. It is therefore desirable to reduce residual levels of colored impurities.

The object of the invention is to provide 3-amino-2-cyclohexan-1-ylidene derivatives represented by the following formula (1) which no longer display the disadvantages described above and which, in particular, possess improved color properties. It is therefore also the object of the present invention to provide an improved process for the purification and isolation of such merocyanine compounds that minimizes discolorations in the final application system.

This object is achieved in accordance with the present invention by means of crystallization of the merocyanine compounds in a specific solvent or solvent mixture.

It has surprisingly been found that these objects can be achieved by a process for preparing a crystalline merocyanine compound comprising the steps of:
(a) dissolving a merocyanine compound in an organic, polar solvent,
(b) causing crystallization of the merocyanine compound from the solution obtained in step (a), and
(c) isolating the merocyanine compound from the crystallization mixture of step (b), wherein the process is performed at a pH below 7 according to the following options
  (i) by adding an acid A1 in step (a),
  (ii) by adding an acid A2 in step (b), or
  (iii) by adding an acid A1 in step (a) and an acid A2 in step (b).

The inventors surprisingly found that by a process for preparing a crystalline merocyanine compound as defined above the therewith obtained merocyanine crystals possess a Gardner Index of less than 5, measured on a Spectrophotometer PE Lambda 650 according to DIN EN ISO 4630. Further, the therewith achieved merocyanine crystals surprisingly possess a superior purity, as well as an improved transmission value at 460 nm, preferably higher than 90%.

Thus, according to one embodiment, the present invention relates to an improved process for preparing a crystalline merocyanine compounds of formula

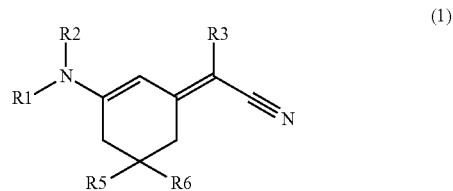

(1)

wherein
$R_1$ and $R_2$ independently of each other are hydrogen; $C_1$-$C_{22}$-alkyl, $C_2$-$C_{22}$-alkenyl, $C_2$-$C_{22}$-alkynyl, $C_3$-$C_{22}$-cycloalkyl, or $C_3$-$C_{22}$-cycloalkenyl, wherein the aforementioned moieties are optionally interrupted by one or more —O— and/or substituted by one or more OH;
$R_3$ is (C=O)$OR_4$, or (C=O)$NHR_4$;
$R_4$ is $C_1$-$C_{22}$-alkyl, $C_2$-$C_{22}$-alkenyl, $C_2$-$C_{22}$-alkynyl, $C_3$-$C_{22}$-cycloalkyl, or $C_3$-$C_{22}$-cycloalkenyl, wherein the aforementioned moieties are optionally substituted by one or more OH and/or interrupted by one or more —O—; and
$R_5$ and $R_6$ independently of each other are hydrogen, or $C_1$-$C_{12}$-alkyl.

In a further aspect, the present invention relates to crystals of a merocyanine compound, obtainable by a process according to the inventive process for preparing a crystalline merocyanine compounds as described herein.

In another aspect, the present invention relates to a merocyanine compound, having a Gardner Index, measured on a Spectrophotometer PE Lambda 650 according to DIN EN ISO 4630, of less than 5.

In another aspect, the present invention relates to a method to reduce residual levels of colored impurities in a merocyanine compound by a process as described herein.

In a further aspect, the present invention relates to the use of crystals obtainable by a process according to the inventive process for preparing a crystalline merocyanine compounds as described herein in cosmetic formulations or in packagings.

Merocyanine compounds of formula (1) are exemplarily prepared by reacting a solution of 1-aminocyclohexanone-3, having formula (2), wherein $R_1$, $R_2$, $R_5$ and $R_6$ are defined as in formula (1) with dimethylsulfate or other suitable alkylating agents and subsequent reaction with a suitable methylene-active compound of formula (3), wherein $R_3$ is defined as in formula (1), as described for example in U.S. Pat. No. 4,749,643, WO 2007/071582 A1, WO 2009027258 A2 or in IP-COM000225139D.

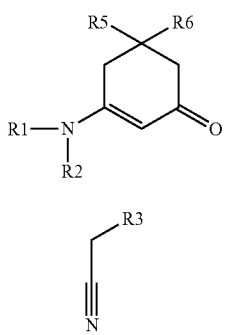

(2)

(3)

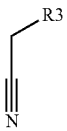

The crude merocyanine product, having formula (1), may be obtained from the reaction mixture through standard product isolation procedures, for example, liquid-liquid separation, filtration, column chromatography, crystallization by cooling, by addition of a poor solvent to the reaction mixture, by distillation, or a combination of these isolation methods.

Before describing in detail exemplary embodiments of the present invention, definitions important for understanding the present invention are given.

As used in this specification and in the appended claims, the singular forms of "a" and "an" also include the respective plurals unless the context clearly dictates otherwise. In the context of the present invention, the term "about" denotes an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%. It is to be understood that the term "comprising" is not limiting. For the purposes of the present invention the term "consisting of" is considered to be a preferred embodiment of the term "comprising of". If hereinafter a group is defined to comprise at least a certain number of embodiments, this is meant to also encompass a group, which preferably consists of these embodiments only. Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. In case the terms "first", "second", "third" or "(a)", "(b)", "(c)", "(d)", "(i)", "(ii)" etc. relate to steps of a method or use or assay there is no time or time interval coherence between the steps, i.e. the steps may be carried out simultaneously or there may be time intervals of seconds, minutes, hours, days, weeks, months or even years between such steps, unless otherwise indicated in the application as set forth herein above or below. It is to be understood that this invention is not limited to the particular methodology, protocols, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

The term "crude merocyanine product" and "crude merocyanine material" refers to the merocyanine compound, which is added in step (a) of the process for preparing a crystalline merocyanine compound, thus to the merocyanine compound obtained via e.g. a multi-step sequence before the crystallization process according to the present invention takes place. The crude merocyanine product may be purified after the multi-step sequence synthesis by any other possible purification method before performing the crystallization process according to the present invention. The crystallization process according to the present invention may however also be performed directly after obtaining the crude merocyanine product after the multi-step sequence synthesis, without any prior purification method.

The term "crystallization mixture" refers to the total weight-% (wt.-%) of the mixture comprising all components at that certain step within the process.

The organic moieties mentioned in the above definitions of the variables are collective terms for individual listings of the individual group members. The prefix $C_n$-$C_m$ indicates in each case the possible number of carbon atoms in the group.

With respect to the variables, the particularly preferred embodiments of the merocyanine compounds correspond to those of the compounds of the formula (1).

The variables of the compounds of the formula (1) have the following meanings, these meanings, both on their own and in combination with one another, being preferred embodiments of the compounds of the formula

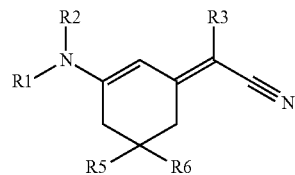

(1)

wherein $R_1$ and $R_2$ independently of each other are hydrogen; $C_1$-$C_{22}$-alkyl, $C_2$-$C_{22}$-alkenyl, $C_2$-$C_{22}$-alkynyl, $C_3$-$C_{22}$-cycloalkyl, or $C_3$-$C_{22}$-cycloalkenyl, wherein the aforementioned moieties are optionally interrupted by one or more —O— and/or substituted by one or more OH;

$R_3$ is (C=O)OR$_4$, or (C=O)NHR$_4$;

$R_4$ is $C_1$-$C_{22}$-alkyl, $C_2$-$C_{22}$-alkenyl, $C_2$-$C_{22}$-alkynyl, $C_3$-$C_{22}$-cycloalkyl, or $C_3$-$C_{22}$-cycloalkenyl, wherein the aforementioned moieties are optionally substituted by one or more OH and/or interrupted by one or more —O—; and $R_5$ and $R_6$ independently of each other are hydrogen, or $C_1$-$C_{12}$-alkyl.

The term "$C_1$-$C_{22}$-alkyl" as used herein denotes in each case a straight-chain or branched alkyl group, such as methyl, ethyl, n-propyl, isopropyl, n-butyl, sec-butyl, isobutyl, tert-butyl, n-pentyl, 2-pentyl, 3-pentyl, 2,2-dimethylpropyl, n-hexyl, n-octyl, 1,1,3,3-tetra-methylbutyl, 2-ethylhexyl, nonyl, decyl, n-octadecyl, eicosyl or dodecyl.

The term "$C_2$-$C_{22}$-alkenyl" as used herein denotes in each case a straight-chain or branched alkenyl group, having at least one singly unsaturated hydrocarbon radical, i.e. a hydrocarbon radical having at least one carbon-carbon double bond, such as straight-chain $C_2$-$C_{12}$-alkenyl or preferably branched $C_3$-$C_{12}$-alkenyl. Other examples are $C_1$-$C_{12}$-alkyl, like vinyl, allyl, 2-propen-2-yl, 2-buten-1-yl, 3-buten-1-yl, 1,3-butadien-2-yl, 2-cyclobuten-1-yl, 2-penten-1-yl, 3-penten-2-yl, 2-methyl-1-buten-3-yl, 2-methyl-3-buten-2-yl, 3-methyl-2-buten-1-yl, 1,4-pentadien-3-yl, 2-cyclopenten-1-yl, 2-cyclohexen-1-yl, 3-cyclohexen-1-yl, 2,4-cyclohexadien-1-yl, 1-p-menthen-8-yl, 4(10)-thujen-10-yl, 2-norbornen-1-yl, 2,5-norbornadien-1-yl, 7,7-dimethyl-2,4-norcaradien-3-yl or the different isomers of hexenyl, octenyl, nonenyl, decenyl or dodecenyl.

The term "$C_2$-$C_{22}$-alkynyl" as used herein denotes in each case a hydrocarbon radical having at least one carbon-carbon triple bond, wherein the chain may be a straight-chain or branched alkynyl group, such as ethynyl, propargyl (2-propyn-1-yl, also referred to as prop-2-yn-1-yl), 1-propyn-1-yl (also referred to as prop-1-yn-1-yl), 1-methylprop-2-yn-1-yl, 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like.

The term "$C_3$-$C_{22}$-cycloalkyl" as used herein denotes in each case a monocyclic or polycyclic cycloaliphatic group, such as cyclopropyl, cyclobutyl, cyclopentyl, trimethylcyclohexyl or preferably cyclohexyl.

The term "$C_3$-$C_{22}$-cycloalkenyl" as used herein denotes in each case a monocyclic or polycyclic singly unsaturated non-aromatic radical. The cycloalkenyl group may be bonded to the remainder of the molecule via a carbon atom, which forms the double bond, or via a carbon atom, which forms a single bond, preferably via a carbon atom, which forms a double bond. Exemplary cycloalkenyl groups include cyclopropen-1-yl, cyclohexen-1-yl, cyclohepten-1-yl or cycloocten-1-yl.

The term "interrupted by one or more —O—" preferably refers to any ether group such as methoxyethyl, ethoxypropyl, 2-ethoxyethyl, 3-methoxypropyl, 2-butoxyethyl or 2-(2-methoxyethoxy)ethyl.

The term "substituted by one or more OH" preferably refers to "hydroxysubstituted alkyl" such as hydroxymethyl, hydroxyethyl, hydroxypropyl, hydroxybutyl, hydroxypentyl, hydroxyhexyl, hydroxyheptyl, hydroxyoctyl, hydroxynonyl or hydroxydecyl.

The term "aliphatic" can refer to any non-aromatic hydrocarbon group, wherein the constituent carbon atoms can be straight-chain, branched-chain, or cyclic and/or wherein heteroatoms can be bond to the carbon chain. Furthermore, these aliphatic groups can be substituted by one or more, same or different substituents.

Within the meaning of the invention, the term "high purity" refers to a compound, having a purity of at least 90 wt.-%, preferably at least 95 wt.-% and more preferably at least wt.-97%, based on the total weight of the final purified product, wherein the remaining wt.-% correspond to impurities.

The merocyanine compounds of the invention may be in the E,E-, E,Z- or Z,Z-geometrical isomer forms.

In one embodiment, the invention relates to a process for preparing a crystalline merocyanine compound of formula (1), as depicted in the following and abbreviated by MC01-MC10, M15, and M27.

Examples of merocyanines according to the present invention are listed in Table A:

TABLE A

| Compound | Structure |
|---|---|
| MC01 | 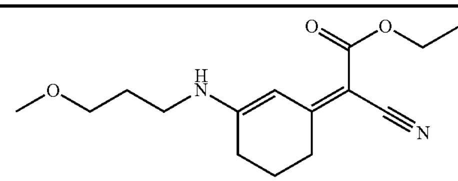 |
| MC02 | 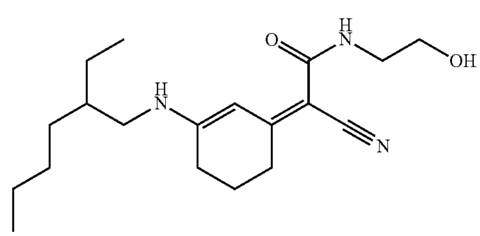 [SMILES: CCCCC(CC)CNC1=C/C(=C(/C#N)C(=O)NCCO)CCC1] |
| MC03 | 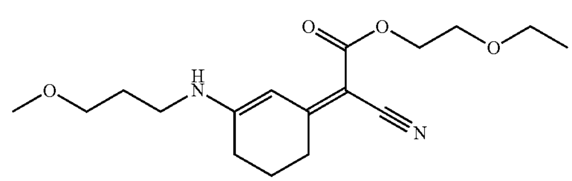 [SMILES: CCOCCOC(=O)/C(C#N)=C1\C=C(NCCCOC)CCC1] |
| MC04 | 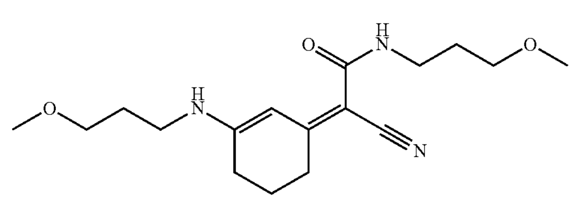 |

TABLE A-continued
| Compound | Structure |
|---|---|
| MC05 | 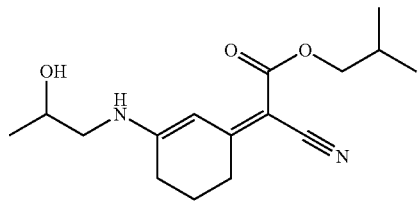 [SMILES: CC(C)COC(=O)/C(C#N)=C1\C=C(NCC(C)O)CCC1] |
| MC06 | 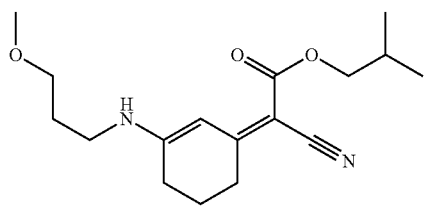 [SMILES: COCCCNC1=C/C(=C(/C#N)C(=O)OCC(C)C)CCC1] |
| MC07 | 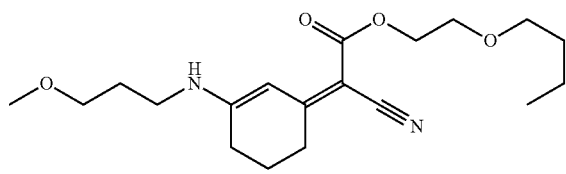 [SMILES: CCCCOCCOC(=O)/C(C#N)=C1\C=C(NCCCOC)CCC1] |
| MC08 | 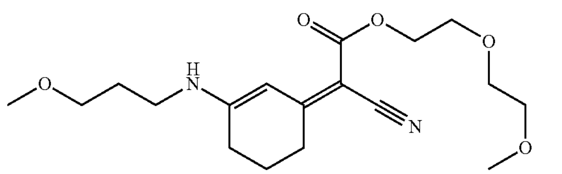 [SMILES: COCCCNC1=C/C(=C(/C#N)C(=O)OCCOCCOC)CCC1] |
| MC09 | 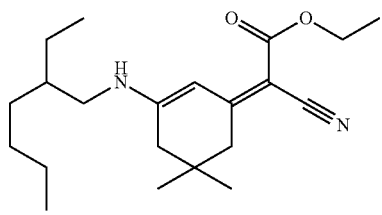 [SMILES: CCCCC(CC)CNC1=C/C(=C(/C#N)C(=O)OCC)CC(C)(C)C1] |
| MC10 | 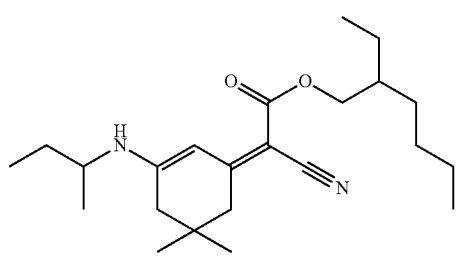 [SMILES: CCCCC(CC)COC(=O)/C(C#N)=C1\C=C(NC(C)CC)CC(C)(C)C1] |

The most preferred merocyanines derivatives of the invention are selected from the group of the following compounds and their E,E-, E,Z- or Z,Z-geometrical isomer forms:

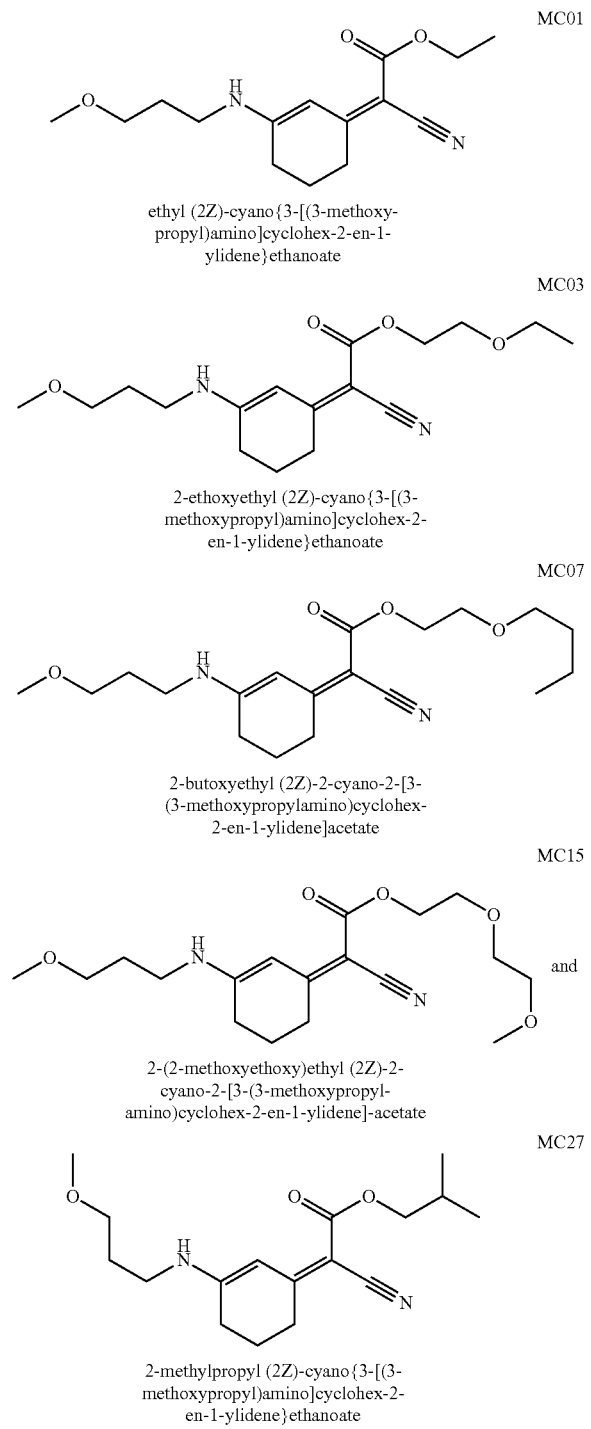

ethyl (2Z)-cyano{3-[(3-methoxy-propyl)amino]cyclohex-2-en-1-ylidene}ethanoate  MC01

2-ethoxyethyl (2Z)-cyano{3-[(3-methoxypropyl)amino]cyclohex-2-en-1-ylidene}ethanoate  MC03

2-butoxyethyl (2Z)-2-cyano-2-[3-(3-methoxypropylamino)cyclohex-2-en-1-ylidene]acetate  MC07

2-(2-methoxyethoxy)ethyl (2Z)-2-cyano-2-[3-(3-methoxypropyl-amino)cyclohex-2-en-1-ylidene]-acetate  MC15

2-methylpropyl (2Z)-cyano{3-[(3-methoxypropyl)amino]cyclohex-2-en-1-ylidene}ethanoate  MC27

According to one particular embodiment of the present invention, the merocyanine compound is 2-ethoxyethyl (2Z)-cyano{3-[(3-methoxypropyl)amino]cyclohex-2-en-1-ylidene}ethanoate.

According to one embodiment of the present invention, the merocyanine compound is provided in step (a) in a concentration in the range from about 50 to about 600 g/L, preferably from about 100 to about 580 g/L, more preferably from about 200 to about 550 g/L.

The weight ratio of the organic, polar solvent to the acid A1 and/or A2 is from about 500:1 to about 0.5:1, preferably from about 400:1 to about 0.8:1, more preferably from about 350:1 to about 1:1.

According to the present invention, the process for preparing a crystalline merocyanine compound comprises the steps of:
(a) dissolving a merocyanine compound in an organic, polar solvent,
(b) causing crystallization of the merocyanine compound from the solution obtained in step (a), and
(c) isolating the merocyanine compound from the crystallization mixture of step (b),
wherein the process is performed at a pH below 7.

In step (a) the merocyanine compound (i.e. the crude merocyanine product) is dissolved in an organic, polar solvent. According to one embodiment of the present invention, the organic, solvent is selected from the group consisting of esters, ketones, ethers, alcohols, and mixtures thereof.

Suitable ester solvents can be methyl formate, ethyl formate, butyl formate, isobutyl formate, methyl acetate, ethyl acetate, propyl acetate, butyl acetate, isobutyl acetate, sec-butyl acetate, amyl acetate, isoamyl acetate, 2-ethylhexyl acetate, octyl acetate, nonyl acetate, hexyl acetate, ethoxypropyl acetate, propionate esters, ethyl 3-ethoxypropionate, butyrate esters, butyl butyrate, ethyl lactate, butyl lactate, butyl glycorate and dimethyl adipate or mixtures thereof. Preferable an ester solvent selected from an formate, acetate or propionate solvent are used.

Also suitable are ketones like acetone, methyl ethyl ketone, methyl propyl ketone, methyl butyl ketone, methyl isobutyl ketone, methyl amyl ketone, ethyl amyl ketone, dipropyl ketone, diisopropyl ketone, diisobutyl ketone, mesityl oxide, cyclohexanone, methylcyclohexanone, isophorone or mixtures thereof.

Ether solvents like diethyl ether, diisopropyl ether, dibutyl ether, di-sec-butyl ether, methyl tert-butyl ether, tetrahydrofurane, 1,4-dioxane, metadioxane and glycol ethers like methyl glycol, 2-ethoxyethanol, 2-propoxyethanol, 2-butoxyethanol, methyl diglycol, butyl diglycol, ethyl glycol, ethyl trigylcol, butyl tetraglycol, dithylene glycol dimethyl ether, butyl trigycol, methoxypropanol, isobutoxypropanol, methyl dipropylene glycol, methoxybutanol and 1,1-dimethoxyethane are suitable.

Suitable alcohol solvents can be methanol, ethanol, propanol, isopropanol, butanol, isobutanol, sec-butanol, tert-butanol, pentanol, amyl alcohol, isoamyl alcohol, hexanol, 2-ethylhexanol, benzyl alcohol, cyclohexanol, methylcyclohexanol, furfuryl alcohol, tetrahydrofurfuryl alco-hol, diacetone alcohol or mixtures thereof. Preferably isopropanol, sec-butanol, tert-butanol, tert-amylalcohol, tert-octylalcohol or mixtures thereof are used.

In a preferred embodiment, the organic, polar solvent is selected from the group consisting of diisopropyl ether, methyl iso-butyl ketone, butyl acetate, isobutyl acetate, n-propyl acetate, isoamyl acetate, ethyl-3-ethoxy propionate, ethyl propionate, 1-methoxy-2-propanol, and mixtures thereof.

The temperature of the obtained solution in step (a) may range from about 0° C. to the boiling point of the solvent or solvent mixture used in this step, preferably from about 20° C. to 100° C., most preferred from 30° C. to 80° C.

In one embodiment, the crude merocyanine product may first be molten and then dissolved in the organic, polar solvent. In this regard, the melt in general needs to first be cooled before the organic, polar solvent is added.

In some cases, it may be expedient to add the acid A1 at step (a) of the process. The acid A1 may then be added to the organic, polar solvent before or after dissolving the merocyanine compound.

In other cases, it may be expedient to add the acid A2 at any other stage of the crystallization step such as in step (b). The acid A2 may exemplarily be added after cooling the crystallization mixture obtained in step (a), after seeding the crude merocyanine solution, or during crystallization into the crystallizing mixture.

In other cases, it may be expedient to add the acid A1 at step (a) of the process and to add the acid A2 at step (b) of the process. Thereby, the acid A1 may be added to the organic, polar solvent before or after dissolving the merocyanine compound and the acid A2 may be added after cooling the crystallization mixture obtained in step (a), after seeding the crude merocyanine solution, or during crystallization into the crystallizing mixture.

Causing the crystallization of the merocyanine compound from the solution obtained in step (a) may be achieved by every common crystallization method, such as addition of solvents to the crystallization mixture wherein the merocyanine compound is less soluble therein, cooling the crystallization mixture, evaporating the solvent from the crystallization mixture, addition of seeding crystals of the merocyanine compound to the crystallization mixture, or mixtures thereof.

In one embodiment of the present invention, the crystallization of the merocyanine compound from the crystallization mixture is caused by
cooling the crystallization mixture,
adding seeding crystals of the merocyanine compound to the crystallization mixture, and/or
adding an acid A2.

The temperature applied in step (b) may range from about $-10°$ C. to below the boiling point of the crystallization mixture, preferably from about $-5°$ C. to $100°$ C. and more preferable from $-5°$ C. to $70°$ C.

Seeding may be performed by the addition of seeding crystals, which may be added in any known way. The seeding crystals may exemplarily be added while stirring the crystallization mixture. Generally, the amount of the seeding crystals added to the crystallization mixture is in the range of from about 0.01 wt.-% to about 2 wt.-%, preferably from about 0.05 wt.-% to about 1.8 wt.-%, based on the total weight of the crystallization mixture.

According to the present invention, an acid A1 and/or an acid A2 is added by the following options:
(i) by adding the acid A1 in step (a),
(ii) by adding the acid A2 in step (b), or
(iii) by adding the acid A1 in step (a) and the acid A2 in step (b),
thereby resulting in a pH of the crystallization mixture of below 7.

Any suitable acid can be used according to the present invention as acid A1 and acid A2. According to the present invention, the acid A1 and the acid A2 are independently selected from the group consisting of organic acids, inorganic acids, and mixtures thereof, wherein any suitable amount may be used. Preferably, the acid A1 and the acid A2 are independently selected from the group consisting of acetic acid, aspartic acid, benzoic acid, boric acid, bromic acid, hydrochloric acid, citric acid, formic acid, gluconic acid, glutamic acid, hydrochloric acid, lactic acid, malic acid, nitric acid, sulfamic acid, sulfuric acid, methane sulfonic acid, toluenesulfonic acid, tartaric acid, phosphoric acid, oxalic acid, malonic acid, succinic acid, glutaric acid, adipic acid, and mixtures thereof. Preferable hydrochloric acid, formic acid or acetic acid are used. Even more preferred are sulfonic acids like methane sulfonic acid.

In one particular embodiment, the acid A1 is formic acid and the acid A2 is methane sulfonic acid.

In one embodiment of the present invention, the process is performed according to option (i). Thus, an acid A1 is added in step (a). In a certain embodiment, the process is performed according to option (i), and the organic, polar solvent is preferably an ester.

In another embodiment of the present invention, the process is performed according to option (ii) or (iii). Thus, an acid A2 is added in step (b) or an acid A1 is added in step (a) and an acid A2 is added in step (b).

The total amount of the acid A1 and/or A2 is in the range from 0.001 wt.-% to 50 wt.-%, preferable from 0.01 wt.-% to 20 wt.-%, and even more preferable from 0.10 wt.-% to 10 wt.-%, based on the total weight of the crystallization mixture.

Step (b) may be performed while stirring. Stirring is conducted during crystallization, as long as the stirring is carried out in a manner which does not interfere with the crystallization process.

When crystallization takes place the stirring time can vary. The stirring time may be in the range from 2 to 30 hours, preferable from 4 to 20 hours, even more preferably from 5 to 15 hours.

In a particular embodiment, the present invention relates to a process, wherein the step (a) of dissolving the merocyanine compound in an organic, polar solvent is performed by heating the mixture to the boiling point, and wherein the step (b) of causing crystallization of the merocyanine compound from the solution obtained in step (a) is performed by cooling the crystallization mixture to a temperature in the range of from $-10°$ C. to below the boiling point of the crystallization mixture.

In another particular embodiment, the present invention relates to a process, wherein the step (a) of dissolving the merocyanine compound in an organic, polar solvent is performed by heating the mixture to the boiling point, and wherein the step (b) of causing crystallization of the merocyanine compound from the solution obtained in step (a) is performed by seeding the crystallization mixture comprising the crude merocyanine solution.

In another particular embodiment, the present invention relates to a process, wherein the step (a) of dissolving the merocyanine compound in an organic, polar solvent is performed by heating the mixture to the boiling point, and wherein the step (b) of causing crystallization of the merocyanine compound from the solution obtained in step (a) is performed by cooling the crystallization mixture to a temperature in the range of from $-10°$ C. to below the boiling point of the crystallization mixture and additional by seeding the crystallization mixture comprising the crude merocyanine solution.

In step (c) the crystalline merocyanine compound may be isolated from the mixture by any conventional methods such as filtration, centrifugation, or evaporation of the solvent. The isolation by filtration or centrifugation is preferred.

The present invention provides a reduction of residual levels of colored impurities in a merocyanine compound by a process as described herein.

In general, the obtained crystals of the merocyanine compound are dried in an optional step (d) after isolation in step (c). Drying may be performed by any known methods such as washing with solvent, drying at room temperature or any higher temperature, freeze-drying, under vacuum, and the like. Drying the under step (c) obtained material at a temperature above 50° C. under vacuum is preferred.

In a particular embodiment, the invention relates to a process as described above, wherein the crystalline merocyanine compound has a Gardner Index, measured on a Spectrophotometer PE (PerkinElmer) Lambda 650 according to DIN EN ISO 4630, of less than 5, preferably of less than 3.2.

The present invention further relates to crystals of a merocyanine compound, obtainable by a process according to the present invention.

In one embodiment, the crystals of the merocyanine compound, obtainable by a process according to the present invention, have a Gardner Index, measured on a Spectrophotometer PE (PerkinElmer) Lambda 650 according to DIN EN ISO 4630, of less than 5, preferably of less than 3.2. In another embodiment, the crystals of the merocyanine compound, obtainable by a process according to the present invention, have a transmission value at 460 nm higher than 90%. In a particular embodiment of the present invention, the crystals of the merocyanine compound, obtainable by a process according to the present invention, have a Gardner Index, measured on a Spectrophotometer PE (PerkinElmer) Lambda 650 according to DIN EN ISO 4630, of less than 5, preferably of less than 3.2 and a transmission value at 460 nm higher than 90%.

The obtained crystals of the merocyanine compound further preferably possess a higher purity.

The crystals of a merocyanine compounds obtained by a process according to the present invention display low discoloring properties. To compare the crystals of a merocyanine compounds with the crude merocyanine products the Gardner Index and % transmission at the wave-length of 460 nm can be determined. The crystals of a merocyanine compounds obtained by the process according to the present invention exhibit significantly lower Gardner Indices which are typically below 3.2 and for many applications desirably below 3.0. In contrast hereto the crude merocyanine materials exhibit Gardner Indices above 5 and higher.

The determined % transmission values of the crystals of a merocyanine compounds obtained by the process according to the present invention measured at the wavelength 460 nm are significantly higher compared to the crude merocyanine materials indicating lower absorption properties in the visible region of the light. While the crystals of a merocyanine compounds according to the present invention display % transmission value of 90% and higher at 460 nm, the crude merocyanine materials have typically a value of 10% and below.

In one embodiment, the present invention relates a crystalline merocyanine compound of formula

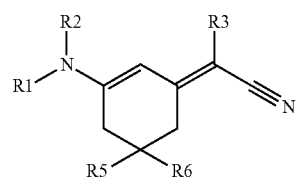

(1)

wherein
$R_1$ and $R_2$ independently of each other are hydrogen; $C_1$-$C_{22}$-alkyl, $C_2$-$C_{22}$-alkenyl, $C_2$-$C_{22}$-alkynyl, $C_3$-$C_{22}$-cycloalkyl, or $C_3$-$C_{22}$-cycloalkenyl, wherein the aforementioned moieties are optionally interrupted by one or more —O— and/or substituted by one or more OH;
$R_3$ is (C=O)O$R_4$, or (C=O)NH$R_4$;
$R_4$ is $C_1$-$C_{22}$-alkyl, $C_2$-$C_{22}$-alkenyl, $C_2$-$C_{22}$-alkynyl, $C_3$-$C_{22}$-cycloalkyl, or $C_3$-$C_{22}$-cycloalkenyl, wherein the aforementioned moieties are optionally substituted by one or more OH and/or interrupted by one or more —O—; and
$R_5$ and $R_6$ independently of each other are hydrogen, or $C_1$-$C_{12}$-alkyl,
wherein the crystalline merocyanine compound has a Gardner Index, measured on a Spectrophotometer PE Lambda 650 according to DIN EN ISO 4630, of less than 5, preferably of less than 3.2.

In another embodiment, the present invention relates a crystalline merocyanine compound of formula

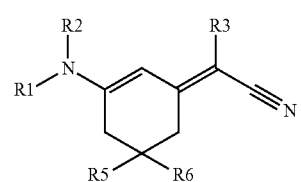

(1)

wherein
$R_1$ and $R_2$ independently of each other are hydrogen; $C_1$-$C_{22}$-alkyl, $C_2$-$C_{22}$-alkenyl, $C_2$-$C_{22}$-alkynyl, $C_3$-$C_{22}$-cycloalkyl, or $C_3$-$C_{22}$-cycloalkenyl, wherein the aforementioned moieties are optionally interrupted by one or more —O— and/or substituted by one or more OH;
$R_3$ is (C=O)O$R_4$, or (C=O)NH$R_4$;
$R_4$ is $C_1$-$C_{22}$-alkyl, $C_2$-$C_{22}$-alkenyl, $C_2$-$C_{22}$-alkynyl, $C_3$-$C_{22}$-cycloalkyl, or $C_3$-$C_{22}$-cycloalkenyl, wherein the aforementioned moieties are optionally substituted by one or more OH and/or interrupted by one or more —O—; and
$R_5$ and $R_6$ independently of each other are hydrogen, or $C_1$-$C_{12}$-alkyl,
wherein the crystalline merocyanine compound has a transmission value at 460 nm higher than 90%.

In yet another embodiment, the present invention relates a crystalline merocyanine compound of formula

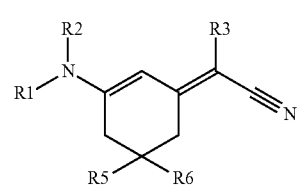

(1)

wherein
$R_1$ and $R_2$ independently of each other are hydrogen; $C_1$-$C_{22}$-alkyl, $C_2$-$C_{22}$-alkenyl, $C_2$-$C_{22}$-alkynyl, $C_3$-$C_{22}$-cycloalkyl, or $C_3$-$C_{22}$-cycloalkenyl, wherein the aforementioned moieties are optionally interrupted by one or more —O— and/or substituted by one or more OH;
$R_3$ is (C=O)O$R_4$, or (C=O)NH$R_4$;
$R_4$ is $C_1$-$C_{22}$-alkyl, $C_2$-$C_{22}$-alkenyl, $C_2$-$C_{22}$-alkynyl, $C_3$-$C_{22}$-cycloalkyl, or $C_3$-$C_{22}$-cycloalkenyl, wherein the aforementioned moieties are optionally substituted by one or more OH and/or interrupted by one or more —O—; and $R_5$ and $R_6$ independently of each other are hydrogen, or $C_1$-$C_{12}$-alkyl, wherein the crystalline merocyanine compound has a Gardner Index, measured on a Spectrophotometer PE Lambda 650 according to DIN EN ISO 4630, of less than 5, preferably of less than 3.2 and wherein the crystalline merocyanine compound has a transmission value at 460 nm higher than 90%.

The crystalline merocyanine compound of formula (1) further preferably possess a higher purity.

The present invention further relates to the use of crystals of the merocyanine compound, obtainable by a process according to the present invention and the use of crystalline merocyanine compounds of formula (1) according to the present invention. In particular, the invention relates to the use of the merocyanine compound, obtainable by a process according to the present invention in cosmetic formulations or in packagings. Further, the invention relates to the use of crystalline merocyanine compounds of formula (1) according to the present invention in cosmetic formulations or in packagings. Preferably, such compounds are used as UV absorber.

The crystals of the merocyanine compound, obtainable by a process according to the present invention and the crystalline merocyanine compound of formula (1) according to the present invention can be mixed with any other UV absorber.

In one embodiment, the crystals according to the present invention are used as single component or in mixture with other UV absorbers in cosmetic formulations, such as skin-care products, bath and shower additives, preparations containing fragrances and odoriferous substances, hair-care products, dentifrices, deodorizing and antiperspirant preparations, decorative preparations, and light protection formulations.

Light protection formulations according to the invention are exemplarily sun milk, lotions, creams, or oils, sun blocks or tropical, pre-tanning preparations or after-sun preparations. In particular, the crystals are used in light protection formulations.

In one embodiment, the crystals according to the present invention are used as single component or in mixture with other UV absorbers in packagings, preferably in transparent packagings, such as for protection of food or pharmaceutical packaging applications.

In another embodiment, the crystals according to the present invention are used as single component or in mixture with other UV absorbers in photographic recording materials.

Due to the improved UV-A and UV-B absorption properties of the crystals according to the present invention, the products, packed with packagings according to the present invention are superiorly protected from UV-A and UV-B radiation.

Analytical Methods:

Gardner Index

The Gardner Index may in general be measured on therefore typically devices. Within the present invention, the Gardner Index is measured on a Spectrophotometer PE (PerkinElmer) Lambda 650 according to DIN EN ISO 4630.

HPLC-Standard Method

Liquid chromatography with DAD-detection was performed.

As column a Zorbax Eclipse XDB-C18 1.8μ, 4.6×100 mm (Agilent) was used.

Mobil Phase A: water and 0.05% formic acid.

Mobil Phase B: acetonitrile and 0.05% formic acid.

The applied standard HPLC gradient is given in Table B.

TABLE B

| Time [min] | Mobil Phase A [%] | Mobil Phase B [%] |
|---|---|---|
| 0 | 90 | 10 |
| 30 | 60 | 40 |
| 40 | 0 | 100 |
| 45 | 0 | 100 |
| 46 | 90 | 10 |
| 53 | 90 | 10 |

The flow was 0.7 mL/min, the injection volume was 3 μL, and the temperature was 47° C. The detection was performed at a wavelength of 230 nm.

% Transmission 460 nm

As spectrophotometer a Lamda 35 and as thermostat a Polystat CC3—Huber G3 was used.

The following parameters were chosen:

Wavelength: 460 nm

Cell type: Quarz, 10 mm

Measuring mode: Transmission

Number of cycle: 1

Response: 2

Lamp: 2

Slit: 2.00 nm

Temperature: 25° C.

Test Solution: 1.00% w/v in ethanol

Reference: (baseline/reference beam): the corresponding blank solution is used

Solvent: Ethanol—anhydrous, denatured, Spectrophotometric-grade; 90%, 5% methanol, 5% iso-propanol—Alfa Aesar Art.Nr. 22931

About 50.0 mg of the corresponding sample was weight into a 5.00 mL volumetric flask and filled up to the marker with ethanol to obtain a 1% w/v solution in ethanol. If necessary, the sample was treated in an ultrasonic bath for 1-2 min.

Purity

The Purity was determined via the above-described HPLC-Standard Method.

The present invention is further illustrated by the following examples.

EXAMPLES

Crystallization of Merocyanine UV Absorbers

Comparative Example: Crystallization of the compound of formula MC03 without acid 30.0 g of compound MC03 (crude product with Gardner Index of 10.7 and 95.4% purity) were dissolved in 70.0 g of n-butyl acetate at 64° C. Cooled to 53° C. with stirring and then seeded with 0.16 g of crystalline compound MC03. Thereafter the temperature was lowered to 10° C., during 15.3 hours. Temperature of 10° C. was maintained for 0.5 hours. The suspension was then transferred to a Büchner funnel and the mother liquor suctioned off. The filter cake was rinsed with 30.0 g of butyl acetate. Then 30.0 g of butyl acetate were added, the cake was re-slurried in the washing liquid by using a spatula and the washing liquor was suctioned off. Finally, the crystals were rinsed with 30.0 g of butyl acetate. The crystals were then dried in a vacuum oven at 85° C. and 20 mbar for 16 hours yielding 25.1 g (87.1% yield) of the pure product of formula MC03. Gardner Index: 7.7, % T 460 nm: 2.4, Purity: 98.8%.

Example 1: Crystallization of the Compound of Formula MC03 with Formic Acid and Methane Sulfonic Acid in an Ether Solvent 50.0 g of compound MC03 (crude product with Gardner Index of 10.7 and 95.8% purity) were transferred to a dropping funnel with heating jacket. The jacket was heated up to 120° C. until the crude product was fully melted. The funnel with the crude product melt was placed on a reaction vessel equipped with an anchor impeller, thermometer, cooling jacket and outlet spindle on the bottom of the vessel. 111.8 g of diisopropyl ether and 35.5 g of formic acid were added to the reactor and heated to 32° C. with steering. During 15 minutes the crude product melt was added keeping the temperature of the mixture in the reactor at 32° C. and maintaining a stirring speed at 350 revolutions/minute. Then 0.64 g of methane sulfonic acid and 1.11 g of crystalline compound MC03 were added to the mixture. The stirrer speed was reduced to 200 rpm and the heating temperature was lowered from 30° C. to 29° C. during 1 hour. Then linear fall in cooling temperature to 19° C. during 240 minutes, then the cooling temperature was lowered to −8° C. during 648 minutes resulting in an internal temperature of −5° C. Internal temperature of −5° C. was maintained for 0.5 hours. The suspension was then transferred to a Büchner funnel and the mother liquor suctioned off. The filter cake was rinsed with 44.4 g of diisopropyl ether/formic acid (95:5). Then the filter cake was washed with 133.2 g of diisopropyl ether in four portions, from which the second portion was used to re-slurry the cake in the washing liquor before suctioning it off. The washed product crystals were dried in a vacuum oven at 65° C. and 20 mbar for 16 hours yielding 39.6 g (80.4% yield) of the crystallized product. Gardner Index=3.0, % T 460 nm: 93.3.

Example 2: Crystallization of the Compound of Formula MC03 with Formic Acid and Methane Sulfonic Acid in an Ether Solvent 26.1 g of compound MC03 (crude product with Gardner Index of 8.6 and 95.9% purity) were dissolved in 17.7 g of formic acid and 55.8 g of diisopropyl ether at 50° C. followed by addition of 0.32 g of methane sulfonic acid. Cooled to 32° C. with stirring and then seeded with 1.25 g of compound MC03. Thereafter the cooling temperature was lowered to −8° C., during 912 minutes. Cooling temperature of −8° C. was maintained for 0.5 hours. The suspension was then transferred to a Büchner funnel and the mother liquor suctioned off. The filter cake was rinsed with 50.0 g of diisopropyl ether/formic acid (95:5). Then the filter cake was washed with 150.0 g of diisopropyl ether in four portions. The washed product crystals were dried in a vacuum oven at 65° C. and 20 mbar for 16 hours yielding 21.5 g (80.9% yield) of the crystallized product. Gardner Index: 2.7, % T 460 nm: 96.1.

Example 3: Crystallization of the Compound of Formula MC03 with Methane Sulfonic Acid in an Ester Solvent 25.0 g of compound MC03 (crude product with Gardner Index of 10.6 and 95.3% purity) were dissolved in 75.0 g of butyl acetate at 54° C. Cooled to temperature of 46° C. followed by the addition of 0.30 g of methane sulfonic acid and 0.13 g of crystalline MC03 for seeding. Then the cooling temperature was lowered to −8° C. resulting in a temperature of −5° C. in the mixture. Cooling temperature of −8° C. was maintained for 0.5 hours. The crystals were then isolated by filtration and washed with 110.0 g of butyl acetate in 3 portions. The product crystals were then dried at 65° C. and 20 mbar for 16 hours yielding 20.0 g (83.3% yield) of the crystalline product of formula MC03. Gardner Index: 2.7, % T 460 nm: 98.2.

Example 4: Crystallization of the Compound of Formula MC03 with Formic Acid in an Ester Solvent 20.0 g of compound MC03 (crude product with Gardner Index of 10.6 and 95.3% purity) were dissolved in 70.0 g of butyl acetate and 10.0 g of formic acid at 49° C. Cooled to temperature of 26° C. followed by the addition 0.10 g of crystalline MC03 for seeding. Then the cooling temperature was lowered to 7° C. resulting in a temperature of 10° C. in the mixture. Cooling temperature of 7° C. was maintained for 0.5 hours. The crystals were then isolated by filtration and rinsed with 40.0 g of diisopropyl ether. Thereafter 50.0 g of diisopropyl ether were added, the cake was re-slurried in the washing liquid by using a spatula and the washing liquor was suctioned off. Finally, the crystals were rinsed with 50.0 g of diisopropyl ether. The crystals were then dried in a vacuum oven at 65° C. and 20 mbar for 64 hours yielding 9.14 g (47.4% yield) of the pure product. Gardner Index: 2.8, % T 460 nm: 97.9.

Example 5: Crystallization of the Compound of Formula MC03 with Methane Sulfonic Acid in an Ester Solvent 20.0 g of compound MC03 (crude product with Gardner Index of 10.6 and 95.3% purity) were dissolved in 80.0 g of n-propyl acetate at 55° C. Cooled to temperature of 41° C. followed by the addition 0.24 g of methane sulfonic acid and 0.10 g of crystals of the formula MC03 for seeding. Then the cooling temperature was lowered to −8° C. resulting in a temperature of −5° C. in the mixture. Cooling temperature of −8° C. was maintained for 0.5 hours. The crystals were then isolated by filtration and rinsed with 30.0 g of cooled n-propyl acetate (temperature of the washing liquor was 5° C.). Thereafter 40.0 g of cooled propyl acetate were added, the cake was re-slurried in the washing liquid by using a spatula and the washing liquor was suctioned off. Finally, the crystals were rinsed with 40.0 g of cooled propyl acetate. The crystals were then dried in a vacuum oven at 65° C. and 20 mbar for 64 hours yielding 14.81 g (77.2% yield) of the pure product. Gardner Index: 2.8, % T 460 nm: 97.4.

Example 6: Crystallization of the Compound of Formula MC03 with Methane Sulfonic Acid in a Ketone Solvent 30.0 g of compound MC03 (crude product with Gardner Index of 10.7 and 95.4% purity) were dissolved in 70.0 g of methyl isobutyl ketone at 49° C. Cooled to temperature of 43° C. followed by the addition 0.36 g of methane sulfonic acid and 0.16 g of MC03 crystals for seeding. Then the cooling temperature was lowered to 7° C. resulting in a temperature of 11° C. in the mixture. Cooling temperature of 7° C. was maintained for 0.5 hours. The crystals were then isolated by filtration using a Büchner funnel equipped with filter paper and rinsed with 30.0 g of cooled methyl isobutylketone (temperature of the washing liquor was 14° C.). Thereafter 30.0 g of cooled methyl isobutyl ketone were added, the cake was re-slurried in the washing liquid by using a spatula and the washing liquor was suctioned off. Finally, the crystals were rinsed with 30.0 g of cooled methyl isobutyl ketone. The crystals were then dried in a vacuum oven at 70° C. and 20 mbar for 2 hours and then at 80° C. and 20 mbar for 16 hours yielding 17.8 g (61.6% yield) of the pure product. Gardner Index: 2.9, % T 460 nm: 96.9.

Example 7: Crystallization of the Compound of Formula MC03 with Methane Sulfonic Acid in an Ester Solvent 30.0 g of compound MC03 (crude product with Gardner Index of 10.7 and 95.4% purity) were dissolved in 70.0 g of isoamyl acetate at 68° C. Cooled to temperature of 58° C. followed by the addition 0.36 g of methane sulfonic acid and 0.16 g of MC03 crystals for seeding. Then the cooling temperature was lowered to 7° C. during 17 hours resulting in a temperature of 10° C. in the mixture. Cooling temperature of 7° C. was maintained for 0.5 hours. The crystals were then isolated by filtration using a Büchner funnel equipped with filter paper and rinsed with 30.0 g of cooled isoamyl acetate (temperature of the washing liquor was 14° C.). Thereafter 30.0 g of cooled isoamyl acetate were added, the cake was re-slurried in the washing liquid by using a spatula and the washing liquor was suctioned off. Finally, the crystals were rinsed with 30.0 g of cooled isoamyl acetate. The crystals were then dried in a vacuum oven at 70° C. and 20 mbar for 2 hours and then at 85° C. and 20 mbar for 16 hours yielding 26.0 g (90.2% yield) of the pure product. Gardner Index: 2.9, % T 460 nm: 96.3.

Example 8: Crystallization of the Compound of Formula MC03 with Methane Sulfonic Acid in an Ester Solvent 36.0 g of compound MC03 (crude product with Gardner Index of 10.7 and 95.4% purity) were dissolved in 60.0 g of ethyl-3-ethoxy propionate at 64° C. Cooled to temperature of 52° C. followed by the addition of a solution consisting of 0.41 g of methane sulfonic acid in 3.00 g of ethyl-3-ethoxy propionate through a funnel which was subsequently rinsed with 1.00 g of ethyl-3-ethoxy propionate. The temperature was lowered to 50° C. and 0.18 g of MC03 crystals were added for seeding. Then the cooling temperature was reduced to −1° C. during 17 hours resulting in a temperature of 5° C. in the mixture. Cooling temperature of −1° C. was maintained for 1 hour. The crystals were then isolated by filtration using a Büchner funnel equipped with filter paper and the mother liquor was suctioned off. The filter cake was then rinsed with 40.0 g of the mother liquor (temperature of the washing liquor was 9° C.). Thereafter 30.0 g of cooled ethyl-3-ethoxy propionate (the temperature of the washing liquor was 9° C.) were added, the cake was re-slurried in the washing liquid by using a spatula and the washing liquor was suctioned off. Finally, the crystals were rinsed with 30.0 g of cooled ethyl-3-ethoxy propionate. The crystals were then dried in a vacuum oven at 85° C. and 20 mbar for 64 hours yielding 29.9 g (86.6% yield) of the pure product. Gardner Index: 2.9, % T 460 nm: 95.3. Purity: 98.1%.

Example 9: Crystallization of the Compound of Formula MC03 with Methane Sulfonic Acid in an Ester Solvent 38.0 g of compound MC03 (crude product with Gardner Index of 10.7 and 95.4% purity) were dissolved in 62.0 g of isobutyl acetate at 75° C. Cooled to temperature of 54° C. followed by the addition of 0.385 g of methane sulfonic acid and 0.18 g of MC03 crystals for seeding. Then the cooling temperature was reduced to 5° C. during 16.3 hours resulting in a temperature of 10° C. in the mixture. Cooling temperature of 5° C. was maintained for 3 hours. The crystals were then isolated by filtration using a Büchner funnel equipped with filter paper and the mother liquor was suctioned off. The filter cake was then rinsed with 40.0 g of the mother liquor (temperature of the washing liquor was 11° C.). Thereafter 30.0 g of cooled isobutyl acetate (the temperature of the washing liquor was 10° C.) were added, the cake was re-slurried in the washing liquid by using a spatula and the washing liquor was suctioned off. Finally, the crystals were rinsed with 30.0 g of cooled isobutyl acetate. The crystals were then dried in a vacuum oven at 85° C. and 20 mbar for 16 hours yielding 33.4 g (91.6% yield) of the pure product. Gardner Index: 2.9, % T 460 nm: 96.0.

Example 10: Crystallization of the Compound of Formula MC03 with Methane Sulfonic Acid in an Ester Solvent 34.0 g of compound MC03 (crude product with Gardner Index of 10.7 and 95.4% purity) were dissolved in 63.0 g of ethyl propionate and 0.7 g of toluene at 65° C. Cooled to temperature of 46° C. followed by the addition of 0.385 g of methane sulfonic acid dissolved in 2.0 g of ethyl propionate through a funnel and subsequently rinsing the funnel with 1.0 g of ethyl propionate. After seeding the mixture with 0.18 g of MC03 crystals the cooling temperature was reduced to 40° C. during 3 hours, then to 20° C. during 5 hours and finally to 0° C. during 4 hours resulting in a temperature of 5° C. in the final mixture. Cooling temperature of 5° C. was maintained for 0.5 hours. The crystals were then isolated by filtration using a Büchner funnel equipped with filter paper and the mother liquor was suctioned off. The filter cake was then rinsed with 40.0 g of the mother liquor (temperature of the washing liquor was 9° C.). Thereafter 30.0 g of cooled ethyl propionate (the temperature of the washing liquor was 9° C.) were added, the cake was re-slurried in the washing liquid by using a spatula and the washing liquor was suctioned off. Finally, the crystals were rinsed with 30.0 g of cooled ethyl propionate. The crystals were then dried in a vacuum oven at 85° C. and 20 mbar for 16 hours yielding 27.7 g (84.9% yield) of the pure product. Gardner Index: 2.7, % T 460 nm: 97.5, purity: 98.0%.

Example 11: Crystallization of the Compound of Formula MC03 with Methane Sulfonic Acid in an Alcohol Solvent 30.0 g of compound MC03 (crude product with Gardner Index of 10.7 and 95.4% purity) were dissolved in 70.0 g of 1-methoxy-2-propanol at 60° C. Cooled to temperature of 36° C. followed by the addition of 0.36 g of methane sulfonic acid and 0.16 g of MC03 crystals for seeding. The cooling temperature was lowered to 7° C. during 9.7 hours, resulting in a temperature of 10° C. in the final mixture. Cooling temperature of 7° C. was maintained for 0.5 hours. The crystals were then isolated by filtration using a Büchner funnel equipped with filter paper and the mother liquor was suctioned off. The filter cake was then rinsed with 30.0 g of cooled 1-methoxy-2-propanol (temperature of the washing liquor was 14° C.). Thereafter 30.0 g of cooled 1-methoxy-2-propanol (the temperature of the washing liquor was 14°

C.) were added, the cake was re-slurried in the washing liquid by using a spatula and the washing liquor was suctioned off. Finally, the crystals were rinsed with 30.0 g of cooled 1-methoxy-2-propanol. The crystals were then dried in a vacuum oven at 85° C. and 20 mbar for 16 hours yielding 12.0 g (41.5% yield) of the pure product. Gardner Index: 2.8, % T 460 nm: 97.4.

Comparison of the color properties, the transmission at 460 nm, and the purity of the crystallized merocyanine compounds according to the present invention (Examples 1-11) with a reference merocyanine crystallized without the presence of an acid (Comparative Example) are listed in Table C:

TABLE C

| Acid | | Gardner Index | % Transmission at 460 nm | % Purity |
|---|---|---|---|---|
| Comparative Example | without acid | 7.7 | 2.4 | 98.8 |
| Example 1 | formic acid + methane sulfonic acid | 3.0 | 93.3 | |
| Example 2 | formic acid + methane sulfonic acid | 2.7 | 96.1 | |
| Example 3 | methane sulfonic acid | 2.7 | 98.2 | |
| Example 4 | formic acid | 2.8 | 97.9 | |
| Example 5 | methane sulfonic acid | 2.8 | 97.4 | |
| Example 6 | methane sulfonic acid | 2.9 | 96.9 | |
| Example 7 | methane sulfonic acid | 2.9 | 96.3 | |
| Example 8 | methane sulfonic acid | 2.9 | 95.3 | 98.1 |
| Example 9 | methane sulfonic acid | 2.9 | 96.0 | |
| Example 10 | methane sulfonic acid | 2.7 | 97.5 | 98.0 |
| Example 11 | methane sulfonic acid | 2.8 | 97.4 | |

The crystallized merocyanine compound in Comparative Example, which was crystallized in an organic, polar solvent without the presence of an acid displays significantly higher yellowing properties described in a high Gardner Index above 5 and a low % transmission value at 460 nm below 10. In contrast hereto the merocyanine compounds in Examples 1 to 11, which were crystallized according to the present invention in the presence of an acid, display significantly better color properties expressed in low Gardner Indices below 3.2 and high % transmission values at 460 nm higher than 90%.

The invention claimed is:

1. A process for preparing a crystalline merocyanine compound comprising the steps of:
   (a) dissolving a merocyanine compound in an organic, polar solvent,
   (b) causing crystallization of the merocyanine compound from the solution obtained in step (a), and
   (c) isolating the merocyanine compound from the crystallization mixture of step (b), wherein the process is performed at a pH below 7 according to the following options
   (i) by adding an acid A1 in step (a),
   (ii) by adding an acid A2 in step (b), or
   (iii) by adding an acid A1 in step (a) and an acid A2 in step (b);
   wherein the acid A1 and the acid A2 are independently selected from the group consisting of organic acids, inorganic acids, and mixtures thereof; and
   wherein the merocyanine compound is represented by formula (1)

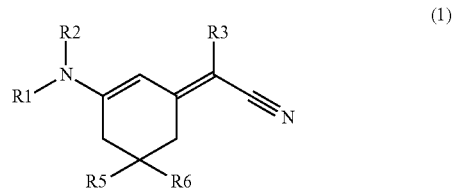

wherein
$R_1$ and $R_2$ independently of each other are hydrogen; $C_1$-$C_{22}$-alkyl, $C_2$-$C_{22}$-alkenyl, $C_2$-$C_{22}$-alkynyl, $C_3$-$C_{22}$-cycloalkyl, or $C_3$-$C_{22}$-cycloalkenyl, wherein the aforementioned moieties are optionally interrupted by one or more —O— and/or substituted by one or more OH;
$R_3$ is (C=O)O$R_4$, or (C=O)NH$R_4$;
$R_4$ is $C_1$-$C_{22}$-alkyl, $C_2$-$C_{22}$-alkenyl, $C_2$-$C_{22}$-alkynyl, $C_3$-$C_{22}$-cycloalkyl, or $C_3$-$C_{22}$-cycloalkenyl, wherein the aforementioned moieties are optionally substituted by one or more OH and/or interrupted by one or more —O—; and
$R_5$ and $R_6$ independently of each other are hydrogen, or $C_1$-$C_{12}$-alkyl.

2. The process according to claim 1, wherein the merocyanine compound is provided in step (a) in a concentration in the range from about 50 to about 600 g/L.

3. The process according to claim 1, wherein the organic, polar solvent is selected from the group consisting of esters, ketones, ethers, alcohols, and mixtures thereof.

4. The process according to claim 1, wherein crystallization of the merocyanine compound from the crystallization mixture is caused by cooling the crystallization mixture, adding seeding crystals of the merocyanine compound to the crystallization mixture, and/or adding an acid A2.

5. The process according to claim 1, wherein the acid A1 is formic acid; and wherein the acid A2 is methane sulfonic acid.

6. The process according to claim 1, wherein the process is performed according to option (ii) or (iii).

7. The process according to claim 1, wherein the process is performed according to option (i), and wherein the organic, polar solvent is an ester.

8. The process according to claim 1, wherein the total amount of the acid A1 and/or A2 is in the range from 0.001 wt.-% to 50 wt. %, based on the total weight of the crystallization mixture.

9. The process according to claim 1, wherein the step (a) of dissolving the merocyanine compound in an organic, polar solvent is performed by heating the mixture to the boiling point, and wherein the step (b) of causing crystallization of the merocyanine compound from the solution obtained in step (a) is performed by cooling the crystallization mixture to a temperature in the range of from −10° C. to below the boiling point of the crystallization mixture.

10. The process according to claim 1, wherein the crystalline merocyanine compound has a Gardner Index, measured on a Spectrophotometer PE Lambda 650 according to DIN EN ISO 4630, of less than 5.

11. The process according to claim 1,
wherein the acid A1 and the acid A2 are independently selected from the group consisting of acetic acid, aspartic acid, benzoic acid, boric acid, bromic acid, hydrochloric acid, citric acid, formic acid, gluconic acid, glutamic acid, lactic acid, malic acid, nitric acid, sulfamic acid, sulfuric acid, methane sulfonic acid, toluenesulfonic acid, tartaric acid, phosphoric acid, oxalic acid, malonic acid, succinic acid, glutaric acid, adipic acid, and mixtures thereof.

12. The process according to claim 1,
wherein the crystalline merocyanine compound has a Gardner Index, measured on a Spectrophotometer PE Lambda 650 according to DIN EN ISO 4630, of less than 3.2.

13. The process according to claim 1,
wherein the organic, polar solvent is selected from the group consisting of diisopropyl ether, methyl isobutyl ketone, butyl acetate, isobutyl acetate, n-propyl acetate, isoamyl acetate, ethyl-3-ethoxy propionate, ethyl propionate, 1-methoxy-2-propanol, and mixtures thereof.

\* \* \* \* \*